(12) United States Patent
Whitehurst et al.

(10) Patent No.: US 7,155,284 B1
(45) Date of Patent: Dec. 26, 2006

(54) TREATMENT OF HYPERTENSION

(75) Inventors: Todd K Whitehurst, Santa Clarita, CA (US); Kelly H. McClure, Simi Valley, CA (US); James R Thacker, Eureka, MO (US); James P McGivern, Stevenson Ranch, CA (US)

(73) Assignee: Advanced Bionics Corporation, Valencia, CA (US)

( * ) Notice: Subject to any disclaimer, the term of this patent is extended or adjusted under 35 U.S.C. 154(b) by 638 days.

(21) Appl. No.: 10/346,538

(22) Filed: Jan. 16, 2003

Related U.S. Application Data

(60) Provisional application No. 60/351,861, filed on Jan. 24, 2002.

(51) Int. Cl.
*A61N 1/18* (2006.01)
(52) U.S. Cl. .......................... 607/44; 604/891.1; 607/3
(58) Field of Classification Search ............... 607/44, 607/3; 604/891.1
See application file for complete search history.

(56) References Cited

U.S. PATENT DOCUMENTS

| | | |
|---|---|---|
| 3,650,277 A | 3/1972 | Sjostrand et al. |
| 4,080,966 A | 3/1978 | McNally et al. |
| 4,308,866 A | 1/1982 | Jelliffe et al. |
| 5,104,859 A | 4/1992 | Sollevi |
| 5,193,539 A | 3/1993 | Schulman et al. |
| 5,193,540 A | 3/1993 | Schulman et al. |
| 5,199,428 A | 4/1993 | Obel et al. |
| 5,312,439 A | 5/1994 | Loeb |
| 5,707,400 A | 1/1998 | Terry, Jr. et al. |
| 5,716,937 A | 2/1998 | Haupert, Jr. |
| 5,733,259 A | 3/1998 | Valcke et al. |
| 5,770,376 A | 6/1998 | Bagrov |
| 5,888,530 A | 3/1999 | Netti et al. |
| 5,910,484 A | 6/1999 | Haupert, Jr. |
| 6,051,017 A | 4/2000 | Loeb et al. |
| 6,178,349 B1 * | 1/2001 | Kieval ............... 607/3 |
| 6,464,687 B1 | 10/2002 | Ishikawa et al. |
| 6,845,267 B1 * | 1/2005 | Harrison et al. ............... 607/3 |
| 2003/0036773 A1 | 2/2003 | Whitehurst et al. |
| 2003/0083698 A1 | 5/2003 | Whitehurst et al. |

FOREIGN PATENT DOCUMENTS

| | | |
|---|---|---|
| WO | WO-98/37926 A1 | 2/1998 |
| WO | WO-98/43700 A1 | 3/1998 |
| WO | WO-98/43701 A1 | 3/1998 |

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

(Continued)

*Primary Examiner*—Jeffrey R. Jastrzab
(74) *Attorney, Agent, or Firm*—Henricks, Slavin & Holmes LLP; Laura Haburay Bishop

(57) ABSTRACT

Treatment of hypertension includes implantation of the discharge portion(s) of a catheter and/or electrical stimulation electrode(s) adjacent the tissue(s) to be stimulated. Stimulation pulses, i.e., drug infusion pulses and/or electrical pulses, are supplied by one or more implanted stimulators, through the catheter and possibly also a lead, tunneled subcutaneously between the stimulator and stimulation site. A microstimulator(s) may also/instead deliver electrical stimulation pulses. Stimulation sites include the carotid sinus and carotid body, among other locations. Treatments include drugs used for acute and/or chronic treatment of hypertension. In a number of embodiments, a need for or response to treatment is sensed, and the electrical and/or infusion pulses adjusted accordingly.

21 Claims, 7 Drawing Sheets

OTHER PUBLICATIONS

Chalmers, et al., "Central Control on Blood Pressure", European Heart Journal, vol. 13 (Suppl A), (1992), pp. 2-9.

Peters, et al., "Temporal and Spatial Summation Caused by Aortic Nerve Stimulation in Rabbits. Effects of Stimulation Frequencies and Amplitudes", Journal of the Autonomic Nervous System, vol. 27(3), (Aug. 1989), pp. 193-205.

Sapru, et al., "Rationale for the Use of Baroceptor Stimulators", J Surg Res, vol.25 (1), (Jul. 1978), pp. 77-82.

Vasquez, et al., "Neural Reflex Regulation of Arterial Pressure in Pathophysiological Conditions: Interplay Among the Baroreflex, the Cardiopulmonary Reflexes and the Chemoreflex", Braz J Med Biol Res, vol. 30(4), (Apr 1997), pp. 521-532.

* cited by examiner

TREATMENT OF HYPERTENSION

The present application claims the benefit of U.S. Provisional Patent Application Ser. No. 60/351,861, filed Jan. 24, 2002, which application is incorporated herein by reference in its entirety.

FIELD OF THE INVENTION

The present invention generally relates to implantable drug delivery and electrical stimulation systems and methods, and more particularly relates to utilizing one or more such implantable devices for treating hypertension.

BACKGROUND OF THE INVENTION

High blood pressure occurs when smaller arteries become abnormally narrow, which causes the blood to exert excessive pressure against the vessel walls. As a consequence, the heart must work harder to maintain the blood flow against this increased resistance. Over an extended period of time, this may lead to enlargement and damage of the heart (cardiac hypertrophy). Although the body can tolerate an increase in blood pressure for months or even years, eventually, damage to blood vessels of the kidneys, the brain, and/or the eyes can occur. Hypertension may also lead to congestive heart failure.

In most hypertensives, both the systolic and diastolic pressures are raised. However, in some older people, "isolated" systolic hypertension may occur. A rise in diastolic pressure used to be considered more serious than a rise in systolic pressure, but now it is accepted that this isolated form of systolic hypertension puts affected people at considerable risk of brain damage due to stroke.

It is estimated that approximately 50 million people in the US have high blood pressure. About half of these people never know it because of the lack of specific symptoms. High blood pressure is therefore sometimes called the "silent killer." It is further estimated that about 50 percent of all hypertensive people are women.

Of the roughly 50 million adult Americans with high blood pressure, only about 27% have their hypertension under control. Of those who have been diagnosed, about 27% are being treated with medications, but are failing to control the condition, and nearly 15% are not participating in any treatment at all.

In most cases of hypertension, the cause is unknown. This is called primary hypertension. In about 5 to 10 percent of people, high blood pressure is a secondary symptom of some other medical condition. For example, there might be an organic cause such as kidney disease, tumor of the adrenal glands, heart defects, or disorders of the nervous system.

Aggressive drug treatment of long-term high blood pressure can significantly reduce the incidence of death from heart disease and other causes in both men and women. In people with diabetes, controlling both blood pressure and blood glucose levels prevents serious complications of that disease. If patients have mild hypertension and no heart problems, then lifestyle changes may suffice to control the condition, if carried out with determination. For more severe hypertension or for mild cases that do not respond to changes in diet and lifestyle within a year, drug treatment is usually necessary. A single-drug regimen can often control mild to moderate hypertension. More severe hypertension often requires a combination of two or more drugs. Prolonged-release drugs are being developed so that they are most effective during early morning periods, when patients are at highest risk for heart attack or stroke.

Hypertensive Medication Therapy

A number of oral and parenteral medications are available for the treatment of hypertension.

Beta-Blockers: Beta-blockers (beta-adrenergic blockers) work by reducing sympathetic nerve input to the heart. Thus, the heart beats less often per minute and with less force. Subsequently, the heart reduces its work, and blood pressure drops. Beta-blockers include propranolol, metoprolol, atenolol, and many others.

Diuretics: Diuretics cause the body to excrete water and salt. This leads to a reduction in plasma volume, which subsequently lowers systemic blood pressure. Diuretics include furosemide, hydrochlorothiazide, and spironolactone.

Angiotensin Converting Enzyme (ACE) Inhibitors: Angiotensin Converting Enzyme (ACE) inhibitors work by preventing the body's production of angiotensin II, a hormone that normally causes blood vessels to narrow. Consequently, the vessels remain wider, which lowers blood pressure. Angiotensin II also normally stimulates the release of another hormone, called aldosterone, which is responsible for the body's retention of sodium. Hence, in addition to creating wider vessels, ACE inhibitors mimic the effect of diuretics to a certain extent. As a result, blood vessels are subject to less pressure, and the heart performs less work. Examples of ACE inhibitors include enalapril, captopril, and lisinopril.

Angiotensin II Antagonists: Relatively new to the world of blood pressure treatment, angiotensin II antagonists are primarily used for patients who develop a cough as a side effect of taking ACE inhibitors. This medication antagonizes angiotensin II, thus inhibiting its effects. Examples include losartan and valsartan.

Calcium Channel Blockers: Calcium channel blockers keep calcium from entering the muscle cells of the heart and blood vessels. The heart and vessels relax, allowing blood pressure to go down. Some calcium channel blockers are nifedipine, verapamil, and diltiazem.

Alpha-Blockers: Alpha-blockers (alpha-adrenergic blockers) target the nervous system to relax blood vessels, allowing blood to pass more easily. Examples of alpha blockers are doxazosin, prazosin, and terazosin.

Alpha-Beta-Blockers: Alpha-beta-blockers (alpha- and beta-adrenergic blockers) basically have the same effect as a combined alpha-blocker and beta-blocker. They target the nervous system to relax the blood vessels, as well as work to slow the heartbeat. As a result, less blood is pumped through wider vessels, decreasing the overall blood pressure. Alpha-beta-blockers include labetalol and carvedilol.

Vasodilators: This category of medication works by relaxing the muscle in the blood vessel wall. Hydralazine and minoxidil are both generic forms of vasodilators.

Hypertensive Medication Efficacy: Research now indicates that beta-blockers, diuretics, and ACE inhibitors all reduce the risk for fatal and nonfatal cardiovascular events. As first-line treatment for most people with hypertension but no comorbid conditions, experts generally recommend beta-blockers or diuretics, which are inexpensive, safe, and effective. Some individuals, however, may have special requirements that call for specific drugs or combinations. Diuretics continue to be the best choice for older adults and for many African-Americans, who are more likely to be salt-sensitive and so respond well to these drugs. Isolated high systolic pressure is usually treated with a diuretic;

adding a beta-blocker may improve outcome. For diabetics, the best drugs are beta-blockers or angiotensin-converting enzyme (ACE) inhibitors. ACE inhibitors have been shown to delay the onset and progression of kidney disease by 30% to 60% and to limit progression of other complications. Beta-blockers are less expensive and one study found that they were as effective as ACE inhibitors in reducing diabetic complications, although more studies are needed. Myocardial infarction (MI) survivors are usually given beta-blockers and sometimes ACE inhibitors to prevent a second MI. People with heart failure should be given ACE inhibitors and diuretics; specific drugs in these classes may be particularly beneficial for these patients because they reduce left ventricle hypertrophy.

It is very important to rigorously maintain a drug regimen. According to a recent study, patients who discontinue antihypertensive therapy, particularly smokers and younger adults, are at a significantly increased risk for stroke. On an encouraging note, one major study found that people taking blood pressure drugs did not experience any greater decline in the general quality of life or daily functioning over five years than did people who were not on blood pressure medication. In all cases, healthy lifestyle changes must accompany any drug treatment.

Hypertensive Medication Side Effects: All drugs used for hypertension have side effects. Common side effects include fatigue, coughing, skin rash, sexual dysfunction, depression, cardiac dysfunction, or electrolyte abnormalities. Some of these are distressing, and ongoing patient compliance may be difficult. Some clinicians have been concerned about the long-term effects of anti-hypertensive drugs on mental processes. A recent study found that brain scans of people who took calcium channel blockers or "loop" diuretics (e.g., furosemide, so called due to diuretic activity on a specific structure in the kidney known as the loop of Henle) detected changes in brain tissue; those who took beta-blockers had no such changes. This is an isolated study and more research is needed to confirm the findings. In spite of worrisome reports of serious side effects associated with some calcium channel blockers, and despite recommendations by a major expert group for wider use of beta-blockers and diuretics, prescriptions for calcium-channel blockers have increased and beta-blockers have decreased over recent years.

Carotid Sinus

The carotid sinus is a dilated area located at the bifurcations of the carotid arteries, and contains baroreceptors that control blood pressure by mediating changes in heart rate. The carotid body is a chemoreceptor located near the bifurcations of the carotid arteries, and monitors changes in oxygen content of the blood and helps control respiratory activity. In most people, the baroreceptors increase their firing rate in response to increased blood pressure, leading to a decrease in heart rate and systemic blood pressure. Both the carotid body and the carotid sinus are supplied with afferent fibers by the carotid sinus nerve, a branch of the glossopharyngeal nerve.

Arterial Baroreceptor Reflex

The maintenance of arterial blood pressure at adequate levels to perfuse the tissues during different conditions is a basic requirement for the survival of mammals, and is achieved by many complex neurohumoral (i.e., neurotransmitter) mechanisms. The main purpose of the baroreflex function is to provide rapid and efficient stabilization of arterial blood pressure on a beat-to-beat basis by means of strategically located arterial sensors which are sensitive to high blood pressure and are known as arterial baroreceptors. The receptor endings of this neural system terminate primarily in the adventitia (i.e., the outer layer) of the carotid sinus and aortic arch with their soma (i.e., cell bodies) located in the petrosal and nodose ganglia, respectively.

At each arterial systole, stretching of these sensors depolarizes them, which triggers action potentials that travel centrally to synapse onto neurons in the nucleus tractus solitarii (NTS, a.k.a. solitary tract nucleus) in the dorsal medulla. These second-order neurons project to the caudal ventrolateral medulla (CVLM) where they synapse with inhibitory neurons that in turn project to the rostral ventrolateral medulla (RVLM) and synapse with bulbospinal sympathoexcitatory neurons located in that area. In parallel, the second-order neurons maintain a tonic excitatory influence upon preganglionic parasympathetic neurons located in the dorsal nucleus of the vagus, rostral ventromedial medulla (RVMM), and mainly in the nucleus ambiguus. Thus, arterial baroreceptors maintain moment-to-moment control of both sympathetic and vagal innervation of the cardiovascular system. Modulation of this system is not restricted to medullary areas of neurons, but is also influenced by supramedullary areas.

Although arterial baroreceptors are capable of acute and chronic resetting to high levels of arterial pressure, baroreflex dysfunction has been reported in arterial hypertension and other cardiovascular diseases both in clinical and experimental hypertension. There are data in the literature showing that the impairment of baroreflex sensitivity can be either a consequence or a cause of arterial hypertension. Changes in vascular structure and distensibility can occur in the aortic arch and sinoaortic vessel walls, for example, with aging, arteriosclerosis, and diabetes, which decrease baroreceptor activity and consequently can contribute to the development of arterial hypertension. There is evidence that human hypertension may be induced or aggravated by impaired baroreceptor reflex control. On the other hand, there is strong evidence that baroreceptor reflex impairment could be a consequence, rather than a cause, of hypertension both in human and experimental animals.

Electrical Stimulation for the Treatment of Hypertension

Electrical stimulation of the carotid sinus was proposed over two decades ago as a therapy for hypertension and angina pectoris. In 1989, Peters, et al. investigated the effects of stimulation frequency and amplitude on hypertension. [See Peters, et al. "Temporal and spatial summation caused by aortic nerve stimulation in rabbits. Effects of stimulation frequencies and amplitudes." *Journal of the Autonomic Nervous System* 1989 August; 27(3):193–205.] In general, increased frequency of electrical stimulation of the carotid sinus leads to decreased systemic blood pressure. However, the absolute frequency required for a given blood pressure may change if the carotid sinus is stimulated for an extended period of time. This study, and other more recent studies involve only acute experiments to demonstrate the potential efficacy of electrical stimulation of the carotid sinus for the treatment of hypertension. Specifically, these systems are not implantable and are not intended for chronic stimulation. In addition, these systems have no drug infusion capabilities or sensing capabilities.

What is lacking in the art, and is therefore needed, are implantable systems and methods capable of chronically providing electrical stimulation of the carotid sinus for treatment of hypertension. Ideal systems and methods also include sensing and/or drug infusion.

BRIEF SUMMARY OF THE INVENTION

The present invention addresses the above and other needs by providing one or more stimulating drugs and/or electrical stimulation to prevent and/or treat hypertension by means of an implantable pump(s) and catheter(s) and/or an implantable signal generator(s) and electrode(s). One or more electrodes are surgically implanted to provide electrical stimulation, and one or more catheters are surgically implanted in the vascular system supplying blood to infuse the stimulating drugs.

The present invention overcomes the shortfalls of prior art devices and methods for the treatment and prevention of hypertension. Specifically, the present invention combines electrical stimulation with delivery of one or more drugs for both acute (on-demand) and chronic (basal or periodic bolus) treatment of hypertension. Additionally, the present invention includes monitoring of blood pressure to achieve an unprecedented level of treatment of hypertension. The treatment is carried out by an implantable pump(s) and catheter(s) having a proximal end coupled to the pump and having a discharge portion for infusing therapeutic dosages of the one or more drugs in a blood vessel(s) or other target site(s) to infuse the drugs. The treatment may alternatively or additionally be carried out by an implantable signal generator(s) and an implantable electrode(s) having a proximal end coupled to the signal generator and having a stimulation portion for electrically stimulating a predetermined stimulation site(s).

The present invention provides antihypertensive therapy carried out by delivery of one or more medications or other substances known to decrease blood pressure. Such medications may include any medication(s) from the following classes of drugs: beta-blockers, diuretics, calcium channel blockers, angiotensin converting enzyme (ACE) inhibitors, angiotensin II antagonists, alpha-blockers, alpha-beta-blockers, and vasodilators. Such substances may also include genes or gene products that lead to a decrease in blood pressure and/or attenuation of the symptoms and pathological consequences of hypertension.

The invention provides antihypertensive therapy carried out chronically through a basal rate and/or periodic bolus delivery of an antihypertensive drug(s). The parameters of delivery may be constant or may be modulated by a clinician, a patient, or other caregiver. The parameters of delivery may also/instead be modulated by sensed data or by another device(s), as discussed herein.

The invention further provides delivery of an antihypertensive drug(s) during an acute emergency, e.g., increased delivery during excessively high blood pressure. Such an increase may reflect an increase in basal rate and/or an increase in bolus dose and/or rate. This increase in delivery may be initiated by a physician, a patient, or other caregiver. This increase in delivery may additionally/alternatively be initiated by sensed data or by another device(s), as discussed herein.

Target sites for drug infusion may include virtually any blood vessel, as antihypertensive therapy is typically delivered systemically. A blood vessel that is unlikely to suffer significant trauma with implantation or attachment of a chronic infusion catheter (e.g., inferior vena cava) is preferred in the case of systemic therapy.

The present invention additionally provides antihypertensive therapy carried out chronically through a constant or periodic electrical stimulation of the carotid sinus and/or other locations. The parameters of stimulation may be constant or may be modulated by a clinician, patient, or other caregiver. Stimulation parameters may also/instead be modulated by sensed data or by another device(s), as discussed herein.

Frequency and/or amplitude of electrical stimulation of the carotid sinus or other locations may be adjusted during an acute emergency, e.g., increased due to excessively high blood pressure. This increase in stimulation may be initiated by a clinician, patient, or other caregiver. This increase in stimulation may additionally or alternatively be initiated by sensed data or by another device(s), as discussed herein.

The invention further provides combinations of the above therapies. In other words, some combination of drug(s) to treat hypertension chronically and/or acutely, and/or drug(s) to treat hypertension chronically and/or acutely may be used to treat some patients. Furthermore, sensed data from sensing means may be used to coordinate the subacute and/or chronic treatment of hypertension by infusion and/or electrical stimulation, and then, when appropriate, the acute treatment of hypertension symptoms. In yet another alternative, this coordination may be controlled by the patient via the patient programmer.

The stimulator used with the present invention preferably possesses one or more of the following properties, among others:

- at least one pump and at least one catheter for delivering a drug or drugs to surrounding tissue and, additionally or alternatively, at least two electrodes for applying stimulating current to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the stimulator;
- means for sensing a need for and/or response to treatment; and
- a form factor making the stimulator implantable in a target area in the body.

A stimulator may operate independently or in a coordinated manner with other implanted stimulators, other implanted devices, and/or with devices external to a patient's body. For instance, a stimulator may incorporate means of sensing hypertension. Sensed information may be used to control the drug and/or electrical stimulation parameters of the stimulator in a closed loop manner. The sensing and stimulating means may be incorporated into a single stimulator or a sensing means may communicate sensed information to at least one stimulator with stimulating means.

For most patients, a continuous or intermittent stimulation throughout the day is needed to provide an adequate amount of treatment. These patients may best utilize a stimulator that has a self-contained power source sufficient to deliver repeated pulses for at least several days and that can be recharged repeatedly, if necessary. In accordance with the teachings of the present invention, the use of a stimulator with a rechargeable battery thus provides these patients the portability needed to free the patient from reliance on RF power delivery. Alternatively, the power source may be a primary battery that may last several years.

For purposes of this patent application, it is sufficient to note that RF controlled stimulators receive power and control signals from an extracorporeal antenna coil via inductive coupling of a modulated RF field. Battery-operated stimulators incorporate a power source within the device itself but rely on RF control, inductive linking, or the like to program stimulus sequences and, if a rechargeable/replenishable power source is used, to recharge/replenish the power source, when needed. In accordance with the present invention, each implanted stimulator may be commanded to produce an electrical and/or infusion pulse of a prescribed magnitude and duration and at a repetition rate sufficient to treat the targeted tissue.

For instance, stimulation may be initiated by start and stop commands from a patient-governed control switch or controller, which may be handheld, containing a microprocessor and appropriate nonvolatile memory, such as electronically erasable programmable read-only-memory (EEPROM). The controller may control the implantable stimulator by any of various means. For instance, the stimulator may sense the proximity of a permanent magnet located in the controller, or may sense RF transmissions from the controller. However, it will be evident to those of skill in circuitry and computing that many different system architectures and components could be used to achieve similar functionality with either a battery-powered or RF-powered stimulator.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
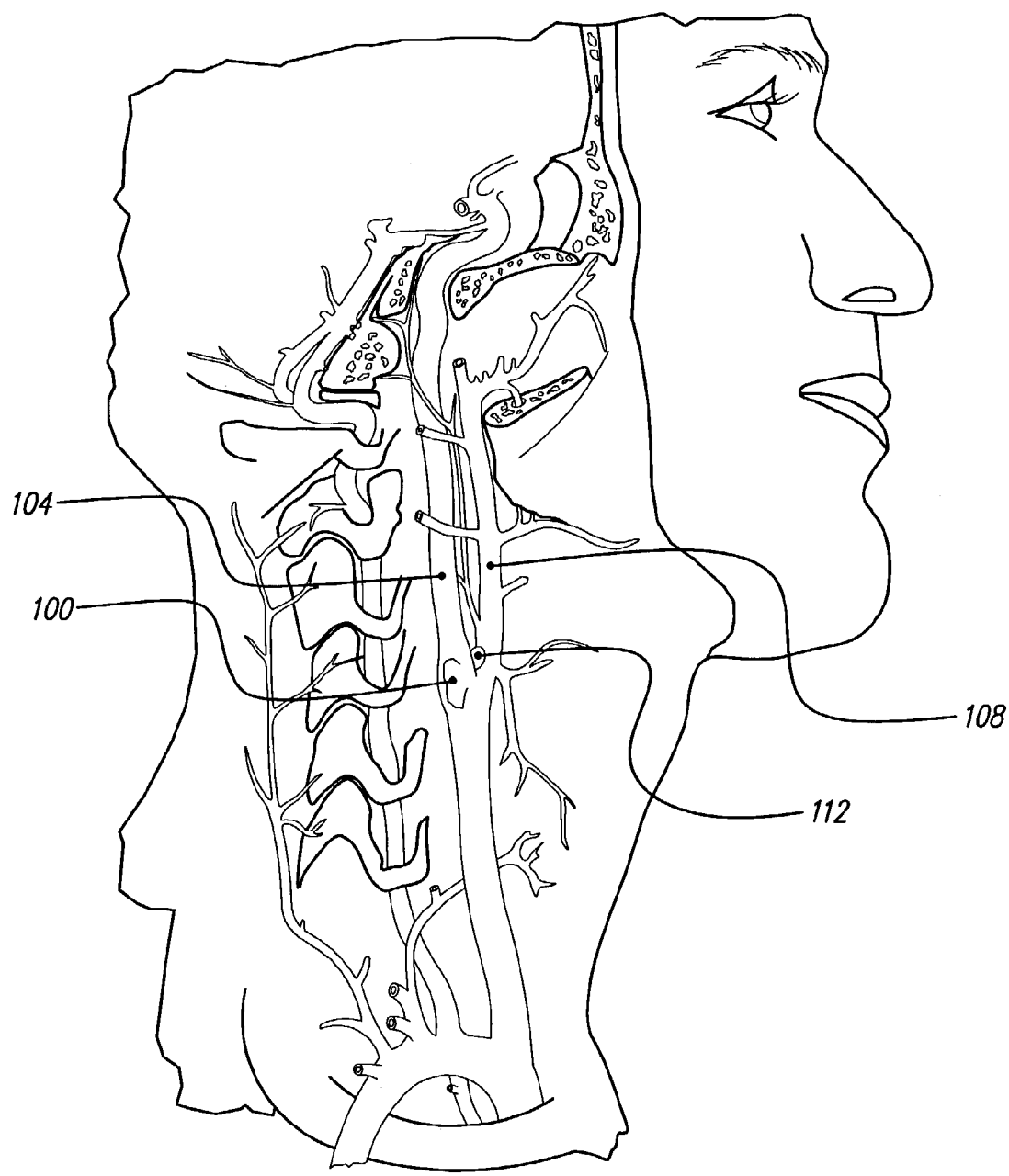
FIG. 1A shows arteries and other structures in the neck area.
Figure 1B:
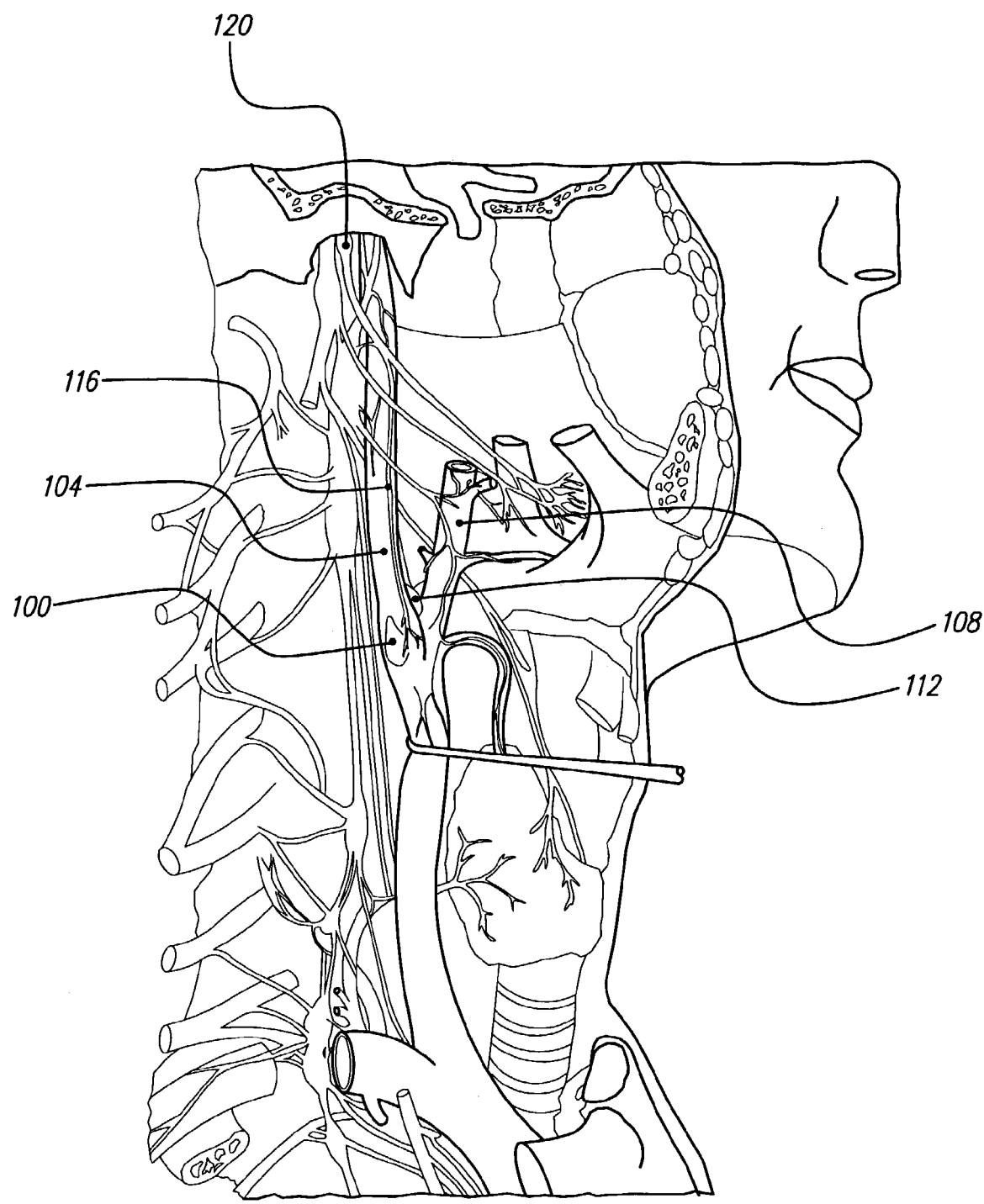
FIG. 1B shows nerves and other structures in the neck area.
Figure 2:
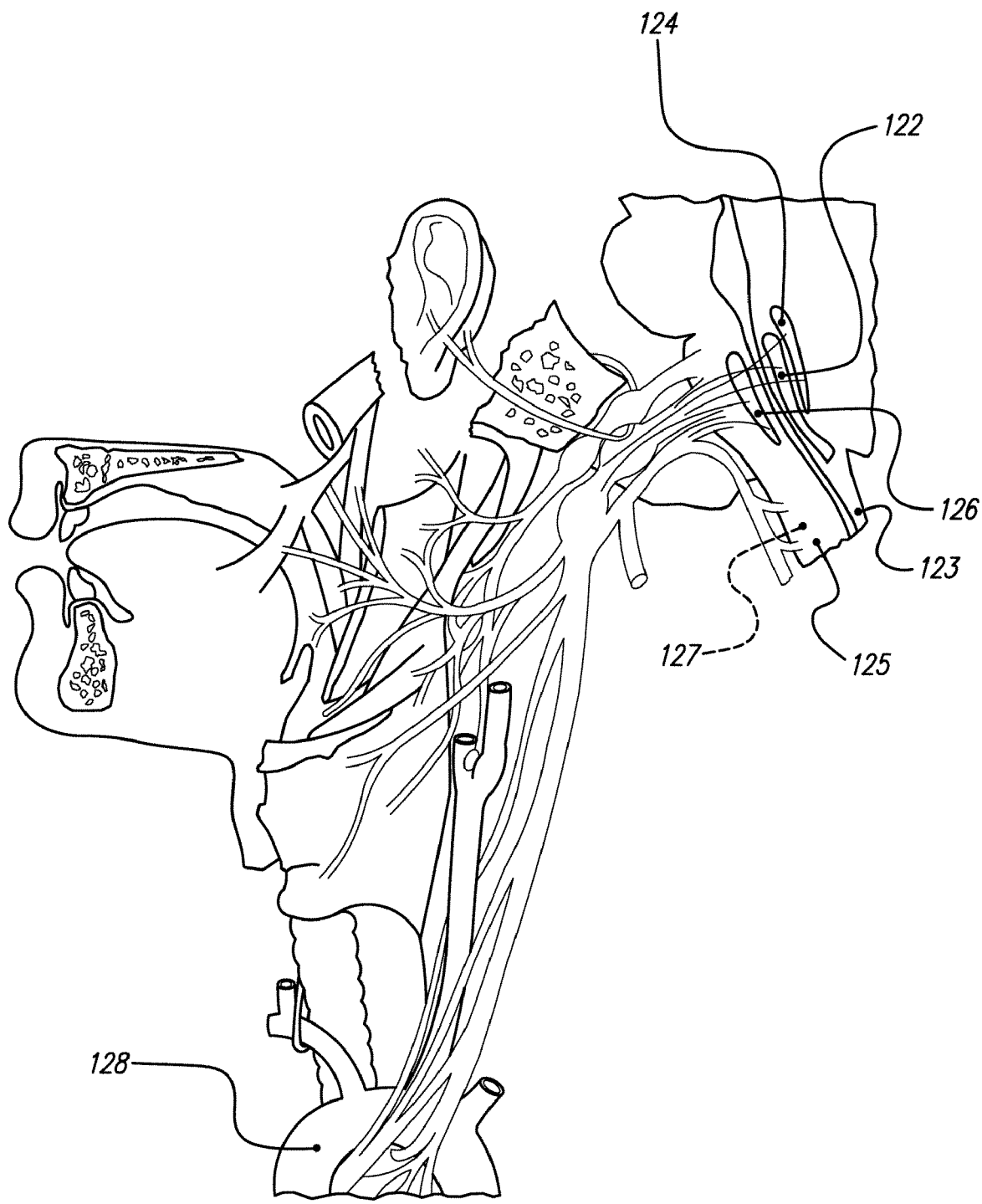
FIG. 2 shows nerves and other structures in the head and neck area.

FIGS. 1A, 1B, and 2 depict arteries, nerves, and other structures in the head and neck area. The carotid sinus 100 is a dilated area located at the bifurcations of the carotid arteries 104 and 108. Carotid sinus 100 contains numerous baroreceptors that help control blood pressure by mediating changes in heart rate. The carotid body 112 is a chemoreceptor located near the bifurcations of carotid arteries 104 and 108. Carotid body 112 monitors changes in the oxygen content of the blood and helps control respiratory activity. In most people, the baroreceptors increase their rate of firing in response to increased blood pressure, and this leads to a decrease in heart rate and a decrease in systemic blood pressure. Carotid body 112 and carotid sinus 100 are supplied with afferent fibers by the carotid sinus nerve 116, a branch of the glossopharyngeal nerve 120.

At each arterial systole, action potentials travel to and synapse on neurons in the nucleus tractus solitarii (NTS 122, a.k.a. solitary tract nucleus) in the dorsal medulla. These second-order neurons project to the caudal ventrolateral medulla (CVLM 123, not shown) where they synapse with inhibitory neurons that in turn project to the rostral ventrolateral medulla (RVLM 125, not shown) and synapse with bulbospinal sympathoexcitatory neurons located in that area. In parallel, the second-order neurons maintain a tonic excitatory influence upon preganglionic parasympathetic neurons located in the dorsal nucleus of the vagus nerve 124, nucleus ambiguus 126, and rostral ventromedial medulla (RVMM 127, not shown).

As mentioned earlier, delivery of one or more stimulating drugs may be used to treat or prevent hypertension. The drugs may be delivered to the left and/or right of one or more of the carotid sinus 100, carotid body 112, NTS 122, dorsal nucleus of the vagus nerve 124, nucleus ambiguus 126, aortic arch 128 (FIG. 2), CVLM 123, RVLM 125, and RVMM 127. Electrical stimulation may be applied during infusion of one or more stimulating drugs or may be applied separately, e.g., to one or more of the carotid sinus 100. As used herein, stimulate, stimulation, and stimulating refer to infusion of a stimulating drug(s) and/or supplying electrical current pulses. As such, infusion parameters and/or electrical current parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

As used herein, stimulating drugs comprise medications and other pharmaceutical compounds, anesthetic agents, synthetic or natural hormones, neurotransmitters, interleukins, cytokines, lymphokines, chemokines, growth factors, and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

The invention includes at least one stimulator. In the case of drug infusion only, a stimulator may comprise an implantable pump. In the case of electrical stimulation as well, the stimulator may also comprise an implantable pulse/signal generator (IPG). In cases where both electrical stimulation and drug infusion are required or desired, more than one stimulator may be used. Alternatively, a stimulator may provide both electrical stimulation and one or more stimulating drugs.

The present invention includes a stimulator that may be implanted in a surgically-created shallow depression or opening in the neck, thorax, abdomen, or above the buttock, that may conform to the profile of surrounding tissue(s) and/or bone(s), and is small and compact. This may minimize any cosmetic impact, and minimize pressure applied to the skin, which pressure can result in skin erosion or infection. As such, a stimulator of certain embodiments has a diameter of about 75 mm, or only about 65 mm, or even less than about 55 mm. In these configurations, stimulator thickness may be approximately 10–12 mm, or even less than about 10 mm.

Figure 3:
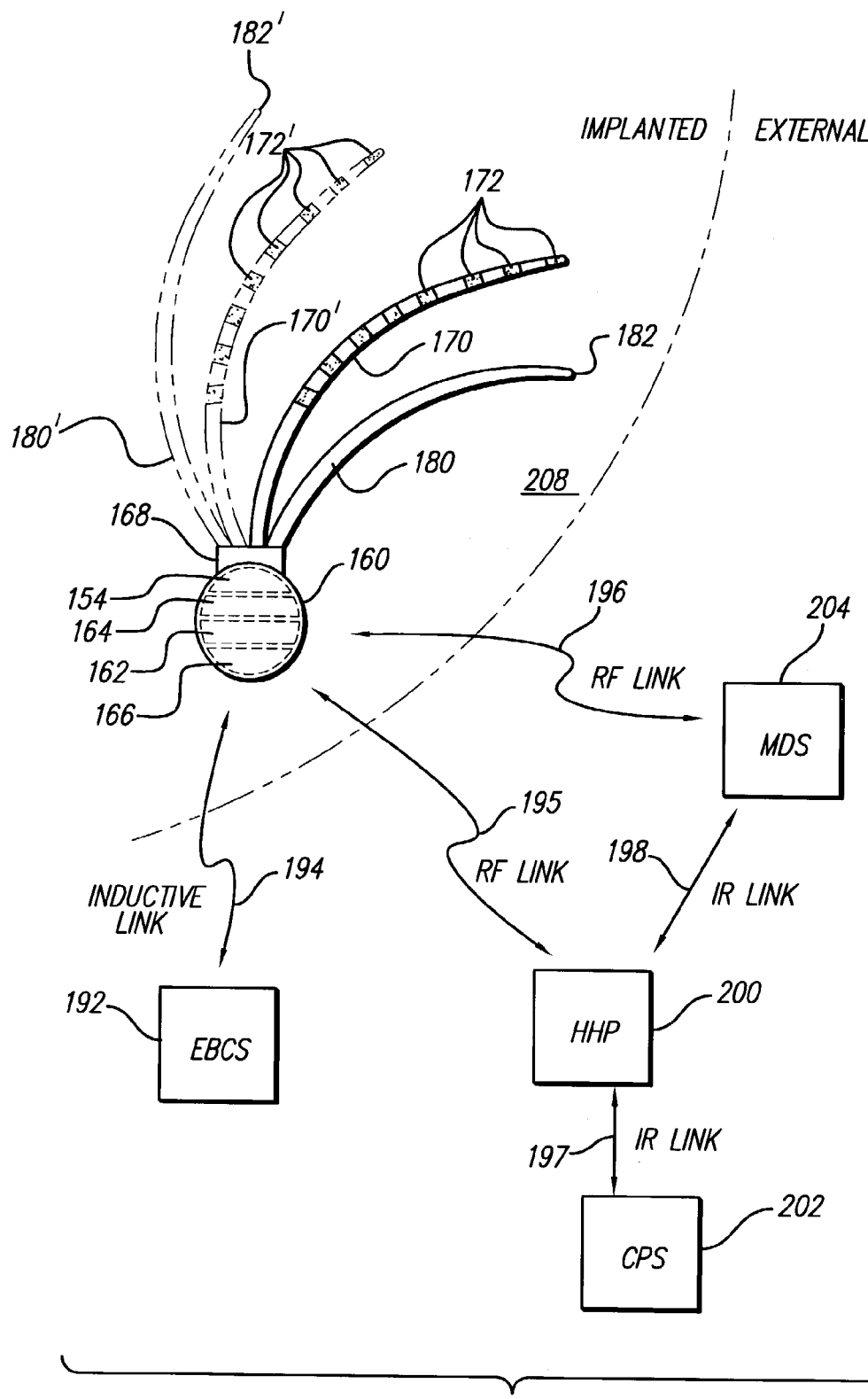
FIG. 3 illustrates internal and external components of an exemplary embodiment of the invention.

In the exemplary embodiment of FIG. 3, one or more catheters 180 and/or one or more leads 170 attach to stimulator 160 and run subcutaneously, such as in a surgically-created tunnel(s), to the tissues to be stimulated. In the case of treatment including electrical stimulation, electrode(s) 172 are carried on lead 170 having a proximal end coupled to stimulator 160. Electrode(s) 172 may include, for instance, a tip electrode and/or one or more ring electrodes, allowing, e.g., temporally synchronized stimulation. The lead contains wires electrically connecting electrodes 172 to stimulator 160. Stimulator 160 contains electrical components 154 that produce electrical stimulation pulses that travel through the wires of lead 170 and are delivered to electrodes 172, and thus to the tissue surrounding electrodes 172. Implantation of such stimulators, leads, and catheters in the locations specified herein is performed as known to those in the art, e.g., as known to interventional cardiologists, who would be able to perform the implantation without undue experimentation.

In the case of treatment alternatively or additionally constituting drug infusion, catheter(s) 180 are coupled at a proximal end to stimulator 160, which contains at least one pump 162 for storing and dispensing one or more drug(s) through the catheter(s) 180. At or along a distal end, catheter 180 has at least one discharge portion 182 for infusing dosages of the one or more drugs into a predetermined site. Catheter 180 may also act as a lead, additionally including electrode(s) 172 at and/or along its distal end.

To protect the components inside stimulator 160, some or all of the case of the stimulator may be hermetically sealed. For additional protection against, e.g., impact, the case may be made of metal (e.g. titanium), ceramic, or the like, which materials are also, advantageously, biocompatible. The material comprising the case of the stimulator 160 may be chosen to limit passage of water vapor, while permitting passage of electromagnetic fields used to transmit data and/or power. In addition, stimulator 160 may be configured to be Magnetic Resonance Imaging (MRI) compatible.

According to embodiments as depicted in FIG. 3, at least one lead 170 and/or catheter 180 is attached to stimulator 160, via a suitable connector(s) 168, if necessary. Each lead includes at least one electrode 172, and may include as many as sixteen or more electrodes 172. Additional leads 170' and/or catheter(s) 180' may be attached to stimulator 160. Hence, FIG. 3 shows (in phantom lines) a second catheter 180', having discharge portion 182', and a second lead 170', having electrodes 172' thereon, also attached to stimulator 160.

Lead(s) 170/170' may, for instance, be less than about 5 mm in diameter, or may be even less than about 1.5 mm in diameter. Electrodes 172, 172' may be made of a noble or refractory metal or compound, such as platinum, iridium, tantalum, titanium, titanium nitride, niobium, or alloys of any of these, in order to avoid corrosion or electrolysis which could damage the surrounding tissues and/or the device. In certain embodiments, stimulator 160 is programmable to produce monopolar electrical stimulation, e.g., using the stimulator case as an indifferent electrode, or bipolar electrical stimulation, e.g., using one of the electrodes of the electrode array as an indifferent electrode. For instance, stimulator 160 may have at least four channels and may drive up to sixteen electrodes or more.

In another alternative, the electrical stimulation is provided by one or more implantable microstimulators, such as of the type referred to as Bionic Neuron (also referred to as BION® microstimulator) devices manufactured by Advanced Bionics of Sylmar, Calif. (see FIG. 4), or similar. The following documents describe various features and details associated with the manufacture, operation, and use of BION implantable microstimulators, and are all incorporated herein by reference:

| Application/Patent/ Publication No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued Jun. 28, 1994 | Implantable Microstimulator |
| U.S. Pat. No. 5,405,367 | Issued Apr. 11, 1995 | Structure and Method of Manufacture of an Implantable Microstimulator |
| PCT Publication WO 98/37926 | Published Sept. 3, 1998 | Battery-Powered Patient Implantable Device |
| PCT Publication WO 98/43700 | Published Oct. 8, 1998 | System of Implantable Devices For Monitoring and/or Affecting Body Parameters |
| PCT Publication WO 98/43701 | Published Oct. 8, 1998 | System of Implantable Devices For Monitoring and/or Affecting Body Parameters |
| U.S. Pat. No. 6,051,017 | Issued Apr. 18, 2000 | Improved Implantable Microstimulator and Systems Employing Same |
|  | Published September, 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

The microstimulator, when used, is preferably implanted with a surgical insertion tool specially designed for the purpose, or may be placed, for instance, via a small incision and through a small cannula. Alternatively, the device may be implanted via conventional surgical methods, or may be inserted using other endoscopic or laparoscopic techniques. A more complicated surgical procedure may be required for fixing the microstimulator in place.

In some embodiments of the instant invention, the microstimulator comprises at least two, leadless electrodes. However, one, some, or all electrodes may alternatively be located at the ends of short, flexible leads as described in U.S. patent application Ser. No. 09/624,130, filed Jul. 24, 2000, which is incorporated herein by reference in its entirety. Other configurations may also permit electrical stimulation to be directed more locally to targeted tissue(s) a short distance from the surgical fixation of the bulk of the implantable stimulator, while allowing elements of the microstimulator to be located in a more surgically convenient site. Such configurations minimize the distance traversed and the surgical planes crossed by the device and any lead(s). In most embodiments, the leads are no longer than about 150 mm.

Stimulator 160 (which herein refers to implantable pump stimulators, IPG stimulators, IPG/pump combination stimulators, microstimulators, and/or other alternative devices known in the art) contains, when necessary and/or desired, electrical circuitry 154 (FIGS. 3 and 4) for receiving data and/or power from outside the body by inductive, radio frequency (RF), or other electromagnetic coupling. In some embodiments, electrical circuitry 154 includes an inductive coil for receiving and transmitting RF data and/or power, an integrated circuit (IC) chip for decoding and storing stimulation parameters and generating stimulation pulses (either intermittent or continuous), and additional discrete components required to complete the circuit functions, e.g. capacitor(s), resistor(s), coil(s), and the like. Circuitry 154 may dictates, for instance, the amplitude and duration of the electrical current pulse, when electrical stimulation is used.

Stimulator 160 also includes, when necessary and/or desired, a programmable memory 164 for storing set(s) of data, stimulation, and control parameters. Among other things, memory 164 may allow electrical and/or drug stimulation and/or control parameters to be adjusted to settings that are safe and efficacious with minimal discomfort for each individual. Specific parameters may provide therapeutic advantages for various types and degrees of hypertension, and regulation of blood pressure, in general. For instance, some patients may respond favorably to intermittent stimulation, while others may require continuous stimulation for treatment and relief. In some embodiments, electrical and drug stimulation parameters are controlled independently, e.g., continuous drug stimulation and no electrical stimulation. However, in some instances, they may advantageously be coupled, e.g., electrical stimulation may be programmed to occur during drug infusion.

Electrical stimulation may be applied in a similar manner as for cardiac pacing and/or cardiac defibrillation. Such stimulation is commonly performed by implantable devices referred to as cardiac pacemakers and implantable cardiac defibrillators (ICDs), respectively. Modern ICDs perform both the pacing and defibrillating functions. Operation of these devices, including stimulation parameters, are well-known to those skilled in the art.

In addition, stimulation and control parameters may be chosen to target specific neural, muscular, and/or other cell populations and to exclude others, or to increase activity in specific neural, muscular, and/or other cell populations and to decrease activity in others. For example, relatively low frequency neurostimulation (i.e., less than about 100–150 Hz) typically has an excitatory effect on surrounding neural tissue, leading to increased neural activity, whereas relatively high frequency neurostimulation (i.e., greater than about 100–150 Hz) typically has an inhibitory effect, leading to decreased neural activity. Similarly, excitatory neurotransmitters (e.g., acetylcholine), agonists thereof, and agents that act to increase levels of an excitatory neurotransmitter(s) (e.g., edrophonium) generally have an excitatory effect on neural tissue, while inhibitory neurotransmitters (e.g., gamma-aminobutyric acid, a.k.a. GABA), generally have an inhibitory effect. However, antagonists of inhibitory neurotransmitters (e.g., bicuculline) and agents that act to decrease levels of an inhibitory neurotransmitter(s) have been demonstrated to excite neural tissue, leading to increased neural activity.

Electrical stimulation parameters of, for instance, the carotid sinus will generally fall in the following ranges:

Frequency: about 10–150 pulses per second (pps).
Duration: about 100–500 microseconds (μs).
Amplitude: about 0.25–10 milliamps (mA).

It is to be understood that the above ranges are not absolute. Rather, they provide a guide for stimulation parameters to be used. An attractive feature of the invention is that the stimulation parameters are programmable and can be adjusted, as required, until an appropriate and efficacious stimulation regime is achieved. For example, relatively low frequency stimulation (i.e., less than about 100–150 Hz) of the carotid sinus is likely to lead to a decrease in systemic blood pressure, while relatively high frequency stimulation (i.e., greater than about 100–150 Hz) of the carotid sinus is likely to lead to an increase in systemic blood pressure.

Figure 4:
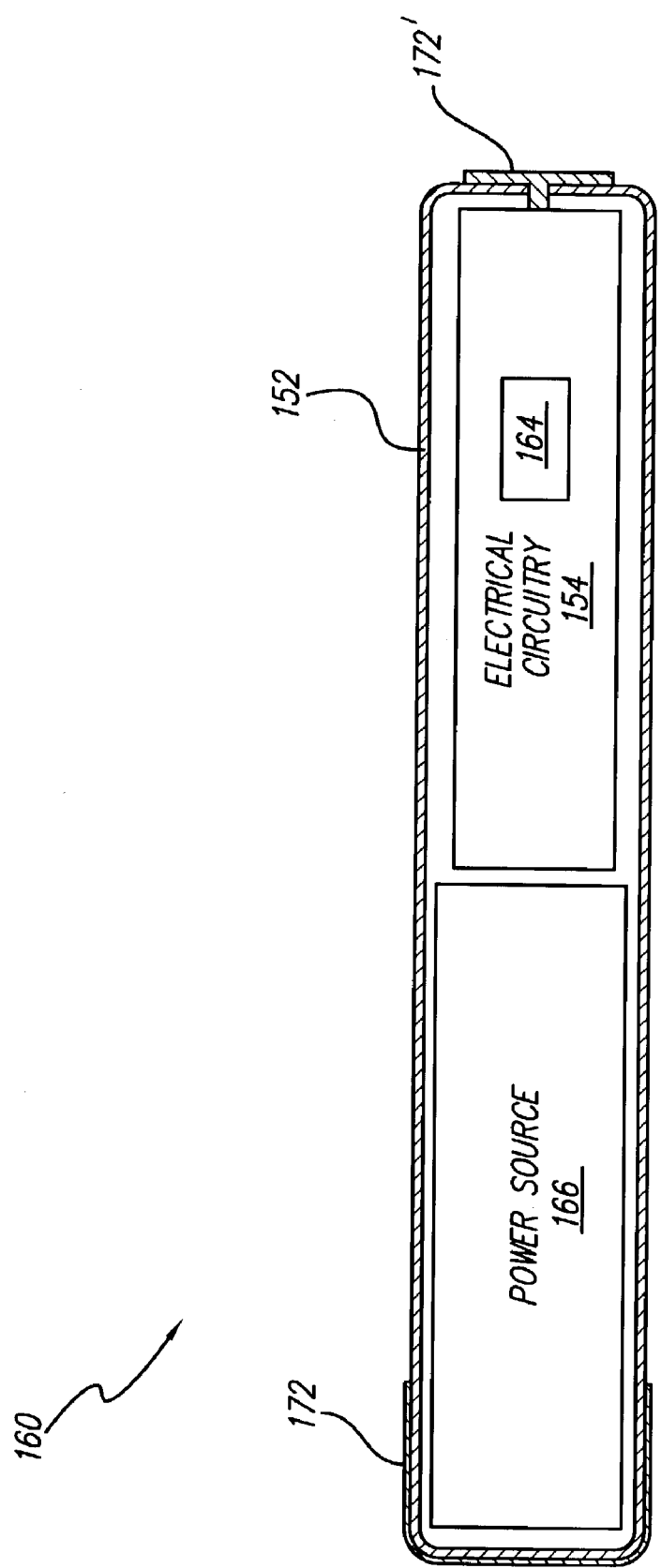
FIG. 4 shows an exemplary configuration of an implantable microstimulator of the present invention.

Some embodiments of stimulator 160 also include a power source and/or power storage device 166 (FIGS. 3 and 4). Possible power options for a stimulation device of the present invention, described in more detail below, include but are not limited to an external power source coupled to the stimulation device (e.g., via an RF link), a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

In embodiments such as depicted in FIG. 3, stimulator 160 includes a rechargeable battery as a power source/storage device 166. The battery is recharged, as required, from an external battery charging system (EBCS) 192, typically through an inductive link 194. In these embodiments, stimulator 160 includes a processor and other circuitry 154 that allow it to generate electrical/infusion pulses that are applied to a patient 208 through electrodes 172 and/or catheter(s) 180 in accordance with a program and stimulation parameters stored in programmable memory 164. As stated earlier, stimulation pulses of drugs include various types and/or rates of infusion, such as intermittent infusion, infusion at a constant rate, and bolus infusion.

According to certain embodiments of the invention, a stimulator operates independently. According to various embodiments of the invention, a stimulator operates in a coordinated manner with other stimulator(s), other implanted device(s), and/or other device(s) external to the patient's body. For instance, a stimulator may control or operate under the control of another implanted stimulator(s), other implanted device(s), or other device(s) external to the patient's body. A stimulator may communicate with other implanted stimulators, other implanted devices, and/or devices external to a patient's body via, e.g., an RF link, an ultrasonic link, a thermal link, and/or an optical link. Specifically, a stimulator may communicate with an external remote control (e.g., patient and/or clinician programmer) that is capable of sending commands and/or data to a stimulator and that may also be capable of receiving commands and/or data from a stimulator.

For example, in some embodiments such as shown in FIG. 3, stimulator 160 of the present invention may be activated and deactivated, programmed and tested through a hand held programmer (HHP) 200 (which may also be referred to as a patient programmer or a remote control and may be, but is not necessarily, hand held), a clinician programming system (CPS) 202 (which may also be hand held), and/or a manufacturing and diagnostic system (MDS) 204 (which may also be hand held). HHP 200 may be coupled to stimulator 160 via an RF link 195. Similarly, MDS 204 may be coupled to stimulator 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to stimulator 160 for programming or diagnostic purposes. MDS 204 may also be coupled to stimulator 160, either directly through RF link 196, or indirectly through IR link 198, HHP 200, and RF link 195.

Figure 5:
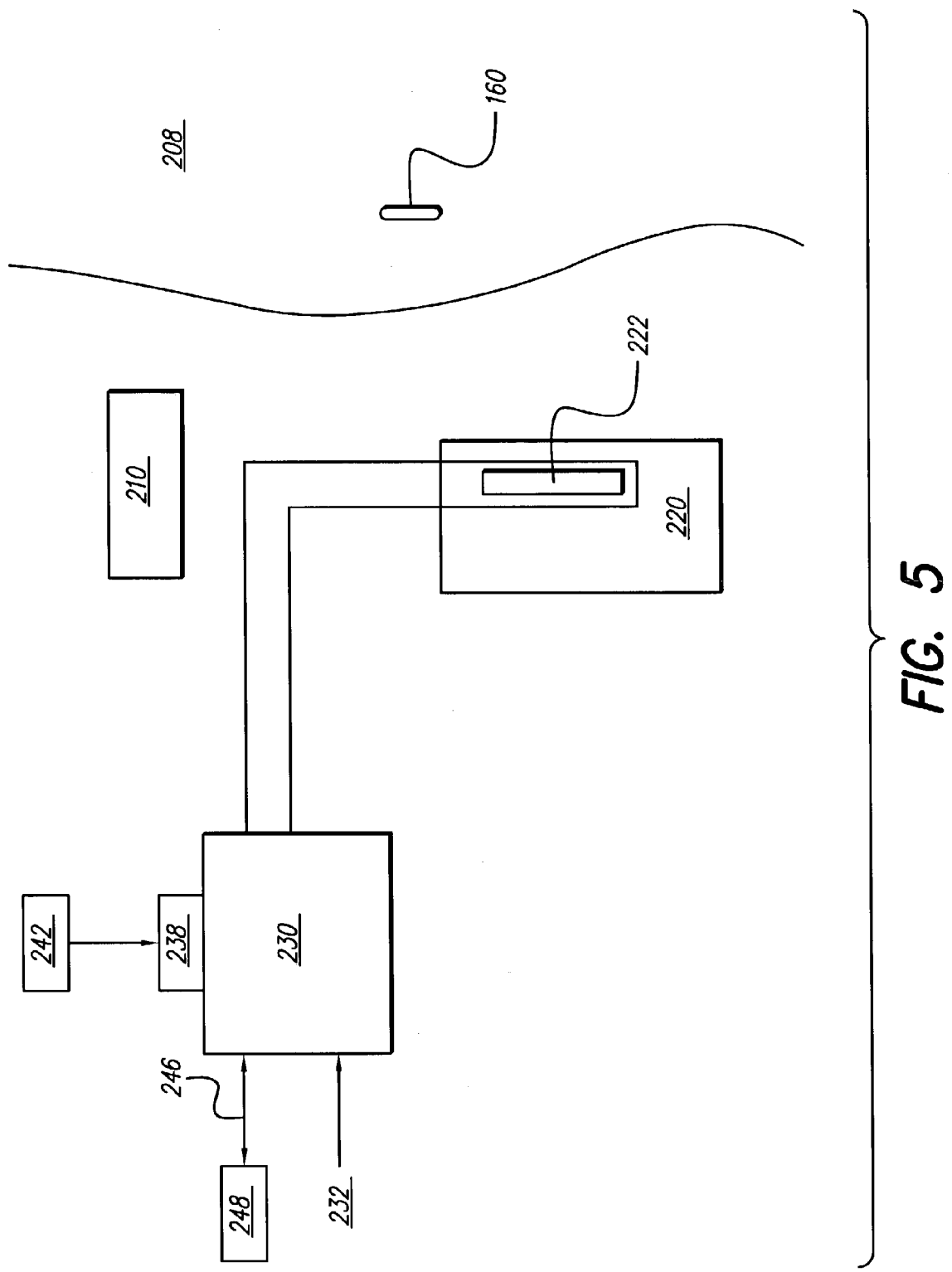
FIG. 5 illustrates internal and external components of an additional exemplary embodiment of the invention.

In certain embodiments, and as illustrated in FIG. 5, the patient 208 switches stimulator 160 on and off by use of controller 210, which may be handheld. Stimulator 160 us operated by controller 210 by any of various means, including stimulator 160 sensing the proximity of a permanent magnet located in controller 210, sensing RF transmissions from controller 210, or the like.

Additional and alternative exemplary external components for programming and/or providing power to various embodiments of stimulator 160 are also illustrated in FIG. 5. When communication with such a stimulator 160 is desired, patient 208 is positioned on or near external appliance 220, which appliance contains one or more inductive coils 222 or other means of communication (e.g., RF transmitter and receiver). External appliance 220 is connected to or is a part of external circuitry appliance 230 which may receive power 232 from a conventional power source. External appliance 230 contains manual input means 238, e.g., a keypad, whereby the patient 208 or a caregiver 242 may request changes in electrical and/or drug stimulation parameters produced during the normal operation of stimulator 160. In these embodiments, manual input means 238 include various electromechanical switches and/or visual display devices that provide the patient and/or caregiver with information about the status and prior programming of stimulator 160.

Alternatively or additionally, electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

One or more of the external appliance(s) may be embedded in a cushion, mattress cover, garment, or the like. Other possibilities exist, including a strap, patch, or other structure(s) that may be affixed to the patient's body or clothing. External appliances may include a package that can be, e.g., worn on the belt, may include an extension to a transmission coil affixed, e.g., with a VELCRO® band or an adhesive, or may be combinations of these or other structures able to perform the functions described herein.

In order to help determine the amount and/or type(s) of stimulating drug(s), and optionally, the strength and/or duration of electrical stimulation required to produce the desired therapeutic effect, in some embodiments, a patient's response to and/or need for treatment is sensed. For instance, any changes in blood pressure produced in response to stimulation may be detected, e.g., via a blood pressure sensor placed in, around, or adjacent to a blood vessel(s). For example, when catheters and/or electrodes of a stimulator are implanted, for example, near the carotid sinus, signals from a pressure sensor built into the stimulator may be used to adjust stimulation parameters based on sensing the systolic and/or diastolic blood pressure in a common carotid artery, external carotid artery, and/or internal carotid artery. (As used herein, "adjacent" or "near" means as close as reasonably possible to target tissue(s), including touching or even being positioned within the tissue, but in general, may be as far as can be reached with the stimulation pulses).

Alternatively, a "stimulator" dedicated to sensory processes communicates with a stimulator that provides the electrical and/or infusion pulses. For instance, a microstimulator, such as a BION, may be used to detect abnormal electrocardiograph (ECG) events or to detect markers of hypertension, e.g., increased blood pressure in a major artery and/or increased blood flow rate in a major artery. As described below, implant circuitry 154 may, if necessary, amplify and transmit these sensed signals, which may be analog or digital. A stimulator or dedicated sensory device may incorporate other means of sensing hypertension or symptoms thereof in order to determine the required stimulation, including sensing brain activity (e.g., EEG), or other measures of the state of the patient, e.g., levels or changes in medication(s), hormone(s), and/or other blood-borne substance(s), including neurotransmitters and/or their associated breakdown products, interleukins, cytokines, lymphokines, chemokines, growth factors, enzymes, or other substances, such as CK-MB, ketones, electrolytes, renin, angiotensin II, and/or other methods mentioned herein, and yet others evident to those of skill in the art upon review of the present disclosure. For instance, one or more Chemically Sensitive Field-Effect Transistors (CHEMFETs), such as Enzyme-Selective Field-Effect Transistors (ENFETs) or Ion-Sensitive Field-Effect Transistors (ISFETs, as are available from Sentron CMT of Enschede, The Netherlands), may be used. The sensed information may be used to control stimulation parameters in a closed-loop manner.

Therefore, in several embodiments of the present invention, a first and second "stimulator" are provided. The second "stimulator" periodically (e.g. once per minute) records common carotid artery blood pressure and transmits it to the first stimulator. The first stimulator uses the sensed information to adjust drug and/or electrical stimulation parameters according to an algorithm programmed, e.g., by a clinician. For example, the infusion rate of a stimulating drug, such as a vasodilator (e.g., hydralazine), an adrenergic antagonist (e.g., carvedilol), and/or a nitrate drug (e.g., nitric oxide or nitroglycerine) may be increased in response to increased common carotid artery blood pressure. In some alternatives, one stimulator performs both the sensing and stimulating functions, as discussed in more detail below.

While a stimulator may incorporate means of sensing hypertension, as described above, e.g., via a blood pressure sensor, ECG, etc., it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted stimulator(s) 160. However, in some cases, it may not be necessary or desirable to include a sensing function or device, in which case stimulation parameters are determined and refined, for instance, by patient feedback, or the like.

Thus, it is seen that in accordance with the present invention, one or more external appliances may be provided to interact with stimulator(s) 160, and may be used to accomplish, potentially among other things, one or more of the following functions:

Function 1: If necessary, transmit electrical power from the external electronic appliance 230 via appliance 220 to stimulator 160 in order to power the device and/or recharge the power source/storage device 166. External electronic appliance 230 may include an automatic algorithm that adjusts drug and/or electrical stimulation parameters automatically whenever the stimulator(s) 160 is/are recharged.

Function 2: Transmit data from the external appliance 230 via the external appliance 220 to stimulator 160 in order to change the parameters of drug and/or electrical stimulation used by stimulator 160.

Function 3: Transmit sensed data indicating a need for treatment or in response to stimulation from stimulator 160 to external appliance 230 via external appliance 220.

Function 4: Transmit data indicating state of the stimulator 160 (e.g., battery level, drug level, electrical stimulation and/or infusion settings, etc.) to external appliance 230 via external appliance 220.

By way of example, referring for example to FIG. 3, a treatment modality for hypertension may be carried out according to the following sequence of procedures:

1. A stimulator 160 is implanted in the thorax, abdomen, back, neck, or other remote location, and its catheter 180 and possibly also lead 170 tunneled so that its catheter discharge portion 182 and possibly also electrodes 172 are located in, around, or adjacent one of the carotid sinuses. If necessary or desired, additional catheters 180' and/or leads 170' may be used so that, for example, catheter discharge portions(s) 182' and/or electrodes 172' may additionally or alternatively be located in, around, or adjacent the contralateral carotid sinus, the aorta, and/or any other major artery.

2. Using HHP 200 described above, stimulator 160 is commanded to infuse a bolus of a vasodilator, e.g., hydralazine or nitroglycerin, possibly while producing a series of electrical stimulation pulses.

3. After each electrical/infusion pulse, series of stimulation pulses, or at some other predefined interval, any change in, e.g., common carotid artery blood pressure resulting from the stimulation is sensed, for instance, by one or more electrodes 172 and/or 172' acting as sensors. If necessary, these responses are converted to data and telemetered to HHP 200, and from there to CPS 202.

4. From the response data received at CPS 202, or from other assessment, the stimulus threshold for obtaining a response is determined and is used by a clinician using CPS 202 and/or HHP 200 to transmit the desired electrical and/or drug stimulation parameters to stimulator 160. Alternatively, the response data are converted, if necessary, and/or used directly by stimulator 160 to modify stimulation parameters in a closed-loop manner.

5. When patient 208 desires to invoke drug and/or electrical stimulation, the patient employs HHP 200 to set stimulator 160 in a state where it delivers a prescribed stimulation pattern from a predetermined range of allowable stimulation patterns.

6. Patient 208 employs HHP 200 to turn off stimulator 160, if desired.

7. Periodically, the patient or caregiver recharges the power source/storage device 166 of stimulator 160, if necessary, using EBCS 192.

In another example, referring now to FIGS. 4 and 5, a treatment modality for hypertension may be carried out according to the following sequence of procedures:

1. A stimulator 160, such a BION microstimulator, is implanted so that its electrodes 172 and 172' are located in, around, or adjacent one of the carotid sinuses. If necessary or desired, additional microstimulators may be used so that, for example, their electrodes may additionally or alternatively be located in, around, or adjacent the contralateral carotid sinus, the aorta, and/or any other major artery.

2. Using Function 2 described above (i.e., transmitting data) of external electronic appliance 230 and external appliance 220, the stimulator 160 is commanded to produce a series of electrical stimulation pulses.

3. After each electrical pulse, series of stimulation pulses, or at some other predefined interval, any change in, e.g., common carotid artery blood pressure resulting from the stimulation is sensed, for instance, by one or more electrodes 172 and/or 172' of a stimulating microstimulator or a "microstimulator" acting as a sensor. If necessary, these responses are converted to data and telemetered out to external electronic appliance 230 via Function 3.

4. From the response data received at external appliance 230, or from other assessment, the stimulus threshold for obtaining a response is determined and is used by a clinician 242 acting directly 238 or by other computing means 248 to transmit the desired electrical stimulation parameters to stimulator 160 in accordance with Function 2. Alternatively, external appliance 230 makes the proper adjustments automatically, and transmits the proper stimulation parameters to stimulator 160. In yet another alternative, stimulator 160 adjusts stimulation parameters automatically based on the sensed response.

5. When patient 208 desires to invoke electrical stimulation and/or drug infusion, patient 208 employs controller 210 to set stimulator 160 in a state where it delivers a prescribed stimulation pattern from a predetermined range of allowable stimulation patterns.

6. Patient 208 employs controller 210 to turn off stimulator 160, if desired.

7. Periodically, the patient or caregiver recharges the power source/storage device 166 of stimulator 160, if necessary, in accordance with Function 1 described above (i.e., transmit electrical power).

For the treatment of any of the various types and degrees of hypertension or symptoms thereof, it may be desirable to modify or adjust the algorithmic functions performed by the implanted and/or external components, as well as the surgical approaches, in ways that would be obvious to skilled practitioners of these arts. For example, in some situations, it may be desirable to employ more than one stimulator 160, each of which could be separately controlled by means of a digital address. Multiple channels and/or multiple patterns of drug and/or electrical stimulation might thereby be programmed by the clinician and controlled by the patient in order to, for instance, deal with complex or multiple symptoms or conditions such as may occur as a result of comorbid diseases, e.g., heart arrhythmia, congestive heart failure, and the like.

In some embodiments discussed earlier, stimulator 160, or two or more stimulators, are controlled via closed-loop operation. A need for and/or response to stimulation is sensed via stimulator 160, or by an additional stimulator (which may or may not be dedicated to the sensing function), or by another implanted or external device. In some cases, the sensing and stimulating are performed by one stimulator. If necessary, the sensed information is transmitted to stimulator 160. In some embodiments, the parameters used by stimulator 160 are automatically adjusted based on the sensed information. Thus, the electrical and/or drug stimulation parameters may be adjusted in a closed-loop manner to provide stimulation tailored to the need for and/or response to the electrical and/or drug stimulation.

Figure 6:
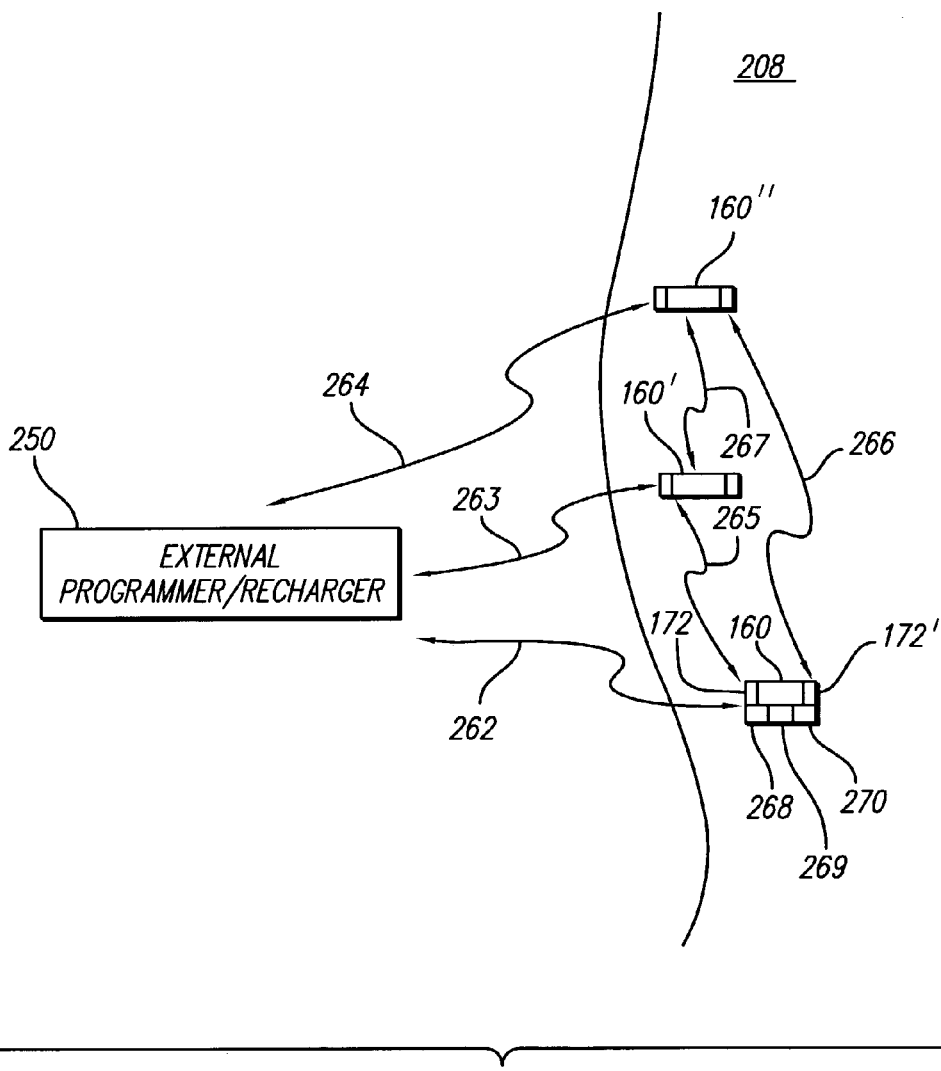
FIG. 6 depicts a system of implantable devices that communicate with each other and/or with external control/programming devices.

For instance, as seen in FIG. 6, a first stimulator 160, implanted beneath the skin of the patient 208, provides stimulation to a first location; a second stimulator 160' provides stimulation to a second location; and a third stimulator 160" provides stimulation to a third location. As mentioned earlier, the implanted devices may operate independently or may operate in a coordinated manner with other similar implanted devices, other implanted devices, or other devices external to the patient's body, as shown by the control lines 262, 263 and 264 in FIG. 6. That is, in accordance with certain embodiments of the invention, an external device, e.g., external controller 250, controls the operation of one or more of the implanted devices 160, 160' and 160". According to various embodiments of the invention, an implanted device, e.g., stimulator 160, may control or operate under the control of another implanted device(s), e.g., stimulator 160' and/or stimulator 160". That is, a device made in accordance with the invention may communicate with other implanted stimulators, other implanted devices, and/or devices external to a patient's body, e.g., via an RF link, an ultrasonic link, a thermal link, an optical link, or the like. Specifically, as illustrated in FIG. 6, stimulator 160, 160', and/or 160", made in accordance with the invention, may communicate with an external remote control (e.g., patient and/or physician programmer 250 and/or the like) that is capable of sending commands and/or data to implanted devices and that may also be capable of receiving commands and/or data from implanted devices.

A stimulator made in accordance with the invention may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

A stimulator made in accordance with the invention further incorporates, in some embodiments, first sensing means 268 for sensing therapeutic effects, clinical variables, or other indicators of the state of the patient, such as blood pressure, ECG, or EEG. The stimulator additionally or alternatively incorporates second means 269 for sensing levels or changes in levels of one or more medications and/or other drugs, hormones, enzymes, interleukins, cytokines, lymphokines, chemokines, growth factors, ketones, and/or electrolytes or other substances in the blood plasma, including CK-MB, neurotransmitters, renin, angiotensin II, and/or their associated breakdown products. The stimulator additionally or alternatively incorporates third means 270 for sensing electrical current levels and waveforms supplied by another source of electrical energy. Sensed information may then be used to control the infusion and/or electrical parameters of the stimulator(s) in a closed loop manner, as shown by control lines 265, 266, and 267. Thus, the sensing means may be incorporated into a device that also includes electrical and/or drug stimulation, or the sensing means (that may or may not have stimulating means), may communicate the sensed information to another device(s) with stimulating means.

Some forms of the present invention use one or more drugs to treat hypertension chronically. According to such embodiments, one or more of the infused drugs is a medication used for chronic treatment of hypertension, such as any medication(s) from the following classes of drugs: beta-blockers, diuretics, calcium channel blockers, angiotensin converting enzyme (ACE) inhibitors, angiotensin II antagonists, alpha-blockers, alpha-beta-blockers, and vasodilators. Such drugs may also include genes or gene products that lead to a decrease in blood pressure and/or attenuation of the symptoms and pathological consequences of hypertension. Such chronic medication may be delivered at a basal rate or via periodic bolus, as programmed by a clinician. The dosage may also be programmed with other drug delivery algorithms by a clinician. As described earlier, if a stimulator has sensing capability or interfaces with another device(s) with sensing capability, such chronic medication delivery may modulated by information sensed by the stimulator or transmitted to the stimulator. For example, the infusion rate of an antihypertensive might be modulated as a result of information from a sensor that senses blood pressure.

Other forms of the present invention use one or more drugs to deliver antihypertensive therapy acutely. According to such embodiments, one or more of the infused drugs is a medication used for acute treatment of hypertension, such as nitroglycerin, nitric oxide, an vasodilator such as hydralazine, and/or a beta-adrenergic antagonist such as labetalol. Such acute medication may be delivered on demand when the patient indicates such delivery is required, such as via depression of an implanted button or via a remote control that is in communication with the stimulator. The control algorithm and/or dosage may be programmed by a clinician, as described earlier. Once again, if a stimulator has sensing capability or interfaces with another device(s) with sensing capability, such acute medication may alternatively be delivered on demand, as programmed by a clinician, when the stimulator senses or is informed of a change in local or systemic blood pressure.

An additional form of the present invention uses electrical stimulation of carotid sinus 100 and/or other locations to treat hypertension chronically. According to such embodiments, constant or periodic electrical stimulation of carotid sinus 100 and/or other location is used for chronic treatment of hypertension. The stimulation parameters may be programmed by a clinician. Again, if a stimulator has sensing capability or interfaces with another device(s) with sensing capability, such chronic stimulation may be modulated by information sensed by or transmitted to the stimulator. For example, the frequency and/or amplitude of electrical stimulation of the carotid sinus 100 might be modulated based on information from a sensor that senses blood pressure.

Yet another form of the present invention uses electrical stimulation of carotid sinus 100 and/or other locations to treat hypertension acutely. According to such embodiments, frequency and/or amplitude of electrical stimulation of carotid sinus 100 and/or other locations is increased for acute treatment of hypertension. Such acute stimulation may be triggered on demand when the patient indicates such delivery is required, such as via depression of an implanted button or via a remote control that is in communication with the stimulator. The control algorithm and/or stimulation parameters may be programmed by a clinician. Again, if a stimulator has sensing capability or interfaces with another device(s) with sensing capability, such acute stimulation may alternatively be delivered, as programmed by a clinician, when the stimulator senses or is informed of an increase in blood pressure.

Yet other forms of the present invention use more than one, even all, of the approaches mentioned above. As such, some combination of drug(s) to treat hypertension chronically and/or acutely, and/or electrical stimulation to treat hypertension chronically and/or acutely may provide the best treatment to some patients. Once again, sensing capabilities described earlier may be used for adjustments to and timing of these treatments.

The drugs and other substances described above may be delivered via approaches, systems, and methods described earlier to one or more of the carotid sinuses, common carotid arteries, internal carotid arteries, external carotid arteries, aorta, and/or any other major artery or arteries. Major arteries are known in the art as the aortic arch, the aorta, the left common carotid artery, the right common carotid artery, the left subclavian artery, the right subclavian artery, the coronary artery, the innominate artery, the renal artery, the superior mesenteric artery, the inferior mesenteric artery, the left iliac artery, and the right iliac artery. Major arterioles are branches of these major arteries. As discussed earlier, electrical stimulation may also be applied during infusion of one or more stimulating drugs.

Furthermore, sensing means described earlier may be used to coordinate the subacute and/or chronic treatment of hypertension by infusion and/or electrical stimulation, and then, when appropriate, the acute treatment of hypertension and/or hypertension symptoms, e.g., sudden or extreme increase in systemic blood pressure, chest pain, headache, blurred vision, or dyspnea (shortness of breath). Alternatively, this coordination may be programmed, and not based on a sensed condition. In yet another alternative, this coordination may be controlled by the patient via the patient programmer.

While the invention herein disclosed has been described by means of specific embodiments and applications thereof, numerous modifications and variations could be made thereto by those skilled in the art without departing from the scope of the invention set forth in the claims.

What is claimed is:

1. A method for treating hypertension, comprising:
    providing at least one stimulator that generates stimulating pulses in accordance with prescribed parameters, which stimulating pulses are infusion pulses;
    providing at least one catheter connected to the at least one stimulator, which catheter includes at least one discharge portion;
    implanting the at least one catheter discharge portion adjacent to at least one tissue to be stimulated;
    implanting the at least one stimulator at a location remote from the at least one tissue to be stimulated;
    tunneling the catheter subcutaneously to the stimulator location; and
    delivering via the infusion pulses at least one drug to the at least one tissue, which tissue comprises at least one portion of the medulla.

2. The method of claim 1 further comprising:
    providing at least one lead connected to the at least one stimulator;
    providing at least one electrode positioned on the at least one lead; and
    delivering electrical stimulating pulses through the at least one lead to tissue adjacent the at least one electrode.

3. The method of claim 2 further comprising implanting more than one stimulator.

4. The method of claim 1 wherein the at least one drug comprises at least one of a beta-blocker, a diuretic, a calcium channel blocker, an angiotensin converting enzyme (ACE) inhibitor, an angiotensin II antagonist, an alpha-blocker, an alpha-beta-blocker, a vasodilator, a gene, and a gene product.

5. The method of claim 1 wherein the at least one drug comprises at least one of nitroglycerin, nitric oxide, a vasodilator, and a beta-adrenergic antagonist.

6. The method of claim 1 further comprising providing at least one sensor to sense a physical condition, and adjusting the stimulating pulses based on the sensed condition.

7. The method of claim 6 further comprising adjusting the stimulation pulses based on the sensed condition, where the sensed condition is at least one of the systolic blood pressure in a major artery, diastolic blood pressure in a major artery, an electrocardiograph (ECG) event, brain activity (e.g., EEG), drug level, change in drug level, hormone level, change in hormone level, enzyme level, change in enzyme level, interleukin level, change in interleukin level, cytokine level, change in cytokine level, lymphokine level, change in lymphokine level, chemokine level, change in chemokine level, growth factor level, change in growth factor level, ketone level, change in ketone level, electrolyte level, change in electrolyte level, CK-MB level, change in CK-MB level, renin level, change in renin level, angiotensin II level, change in angiotensin II level, neurotransmitter level, change in neurotransmitter level, breakdown product level, change in breakdown product level, other blood-borne substance level, and change in other blood-borne substance level.

8. A method for treating hypertension, comprising:
    providing at least one stimulator adapted to generate electrical stimulation pulses and stimulating infusion pulses and having at least one electrode of a size and shape suitable for placement adjacent tissue to be stimulated;
    implanting the at least one electrode adjacent to tissue at least in part responsible for controlling blood pressure;
    providing at least one catheter connected to the at least one stimulator, which catheter includes at least one discharge portion;
    implanting the at least one catheter discharge portion adjacent to tissue at least in part responsible for controlling blood pressure;
    delivering electrical stimulation pulses to the tissue adjacent the at least one electrode, which tissue comprises at least one portion of the medulla; and
    delivering via the stimulating infusion pulses at least one drug to the tissue adjacent to the catheter discharge portion, which tissue comprises at least one portion of the medulla.

9. The method of claim 8 further comprising implanting more than one stimulator.

10. The method of claim 8 further comprising providing at least one sensor to sense a physical condition, and adjusting at least one of the electrical stimulation pulses and the stimulating infusion pulses based on the sensed condition.

11. The method of claim 10 further comprising adjusting at least one of the electrical stimulation pulses and the stimulating infusion pulses based on the sensed condition, where the sensed condition is at least one of the systolic blood pressure in a major artery, diastolic blood pressure in a major artery, an electrocardiograph (ECG) event, brain activity (e.g., EEG), drug level, change in drug level, hormone level, change in hormone level, enzyme level, change in enzyme level, interleukin level, change in interleukin level, cytokine level, change in cytokine level, lymphokine level, change in lymphokine level, chemokine level, change in chemokine level, growth factor level, change in growth factor level, ketone level, change in ketone level, electrolyte level, change in electrolyte level, CK-MB level, change in CK-MB level, renin level, change in renin level, angiotensin II level, change in angiotensin II level, neurotransmitter level, change in neurotransmitter level, breakdown product level, change in breakdown product level, other blood-borne substance level, and change in other blood-borne substance level.

12. The method of claim 8 wherein providing at least one stimulator comprises:
providing a first stimulator having at least one electrode and a size and shape suitable for placement adjacent tissue to be stimulated and adapted to generate electrical stimulation pulses;
providing a second stimulator connected to the at least one catheter and adapted to generate stimulating infusion pulses.

13. The method of claim 12 wherein implanting the at least one stimulator comprises:
implanting the first stimulator adjacent to tissue at least in part responsible for controlling blood pressure; and
implanting the second stimulator.

14. The method of claim 13 wherein
delivering electrical stimulation pulses comprises delivering electrical stimulation pulses from the first stimulator to the tissue adjacent the at least one electrode; and
delivering via the stimulating infusion pulses comprises delivering via the stimulating infusion pulses at least one drug from the second stimulator to the tissue adjacent to the catheter discharge portion.

15. The method of claim 8 wherein
the at least one portion of the medulla to which electrical stimulation pulses are delivered comprises at least one of the nucleus tractus solitarii (NTS), caudal ventrolateral medulla (CVLM), rostral ventrolateral medulla (RVLM), dorsal nucleus of the vagus nerve, nucleus ambiguus, and rostral ventromedial medulla (RVMM); and
the at least one portion of the medulla to which electrical stimulation pulses are delivered comprises at least one of the nucleus tractus solitarii (NTS), caudal ventrolateral medulla (CVLM), rostral ventrolateral medulla (RVLM), dorsal nucleus of the vagus nerve, nucleus ambiguus, and rostral ventromedial medulla (RVMM).

16. The method of claim 1 wherein the at least one portion of the medulla to which infusion pulses are delivered comprises at least one of the nucleus tractus solitarii (NTS), caudal ventrolateral medulla (CVLM), rostral ventrolateral medulla (RVLM), dorsal nucleus of the vagus nerve, nucleus ambiguus, and rostral ventromedial medulla (RVMM).

17. A method for treating hypertension, comprising:
providing at least one implantable stimulator having at least one electrode of a size and shape suitable for placement adjacent tissue to be stimulated, the stimulator being adapted to generate electrical stimulation pulses and stimulating infusion pulses;
implanting the at least one electrode adjacent to tissue at least in part responsible for controlling blood pressure;
providing at least one catheter connected to the at least one stimulator, which catheter includes at least one discharge portion;
implanting the at least one catheter discharge portion adjacent to tissue at least in part responsible for controlling blood pressure;
delivering electrical stimulation pulses to tissue adjacent the at least one electrode, which tissue comprises at least one portion of the medulla; and
delivering via the stimulating infusion pulses at least one drug to the tissue adjacent to the catheter discharge portion, which tissue comprises at least one of the left carotid sinus, the right carotid sinus, the aortic arch, an artery, an arteriole and the vagus nerve.

18. The method of claim 17 wherein the at least one drug comprises at least one of a beta-blocker, a diuretic, a calcium channel blocker, an angiotensin converting enzyme (ACE) inhibitor, an angiotensin II antagonist, an alpha-blocker, an alpha-beta-blocker, a vasodilator, a gene, and a gene product.

19. The method of claim 17 wherein the at least one drug comprises at least one of nitroglycerin, nitric oxide, a vasodilator, and a beta-adrenergic antagonist.

20. The method of claim 17 further comprising providing at least one sensor to sense a physical condition, and adjusting the stimulating pulses based on the sensed condition.

21. The method of claim 17 wherein providing at least one stimulator comprises:
providing a first stimulator having at least one electrode and a size and shape suitable for placement adjacent tissue to be stimulated and adapted to generate electrical stimulation pulses;
providing a second stimulator connected to the at least one catheter and adapted to generate stimulating infusion pulses.

* * * * *